United States Patent
Dukandar et al.

(10) Patent No.: US 8,258,357 B2
(45) Date of Patent: Sep. 4, 2012

(54) PRODUCTION OF PROPYLENE FROM BUTANE

(75) Inventors: Kerman Dukandar, Edison, NJ (US); David Spence, Randolph, NJ (US); Sunil Panditrao, Hackettstown, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 606 days.

(21) Appl. No.: 12/410,851

(22) Filed: Mar. 25, 2009

(65) Prior Publication Data

US 2010/0249471 A1 Sep. 30, 2010

(51) Int. Cl.
  *C07C 6/04* (2006.01)
  *C07C 5/05* (2006.01)
  *C07C 5/327* (2006.01)
(52) U.S. Cl. ......... 585/323; 585/654; 585/259; 585/643
(58) Field of Classification Search .................. 585/323, 585/654, 259, 643
  See application file for complete search history.

(56) References Cited

U.S. PATENT DOCUMENTS

| | | |
|---|---|---|
| 6,075,173 A | 6/2000 | Chodorge et al. |
| 6,207,115 B1 | 3/2001 | Chodorge et al. |
| 6,420,619 B1 | 7/2002 | Gartside et al. |
| 6,743,958 B2 | 6/2004 | Commereuc et al. |
| 7,074,976 B2 | 7/2006 | Powers et al. |
| 7,417,173 B2 | 8/2008 | Crone et al. |
| 2008/0033223 A1* | 2/2008 | Sigl et al. ............. 585/324 |

OTHER PUBLICATIONS

International Search Report and Written Opinion mailed Oct. 18, 2010 in corresponding International Application No. PCT/US2010/028201 (8 pages).
Propylene Plant, Copyright 2002-2007 International Process Plants.

* cited by examiner

*Primary Examiner* — Thuan Dinh Dang
(74) *Attorney, Agent, or Firm* — Osha • Liang LLP

(57) ABSTRACT

This invention relates to an integrated process for the efficient production of olefins from $C_4$ feedstocks comprising butane and more particularly to a method of producing propylene and butadiene. The process combines a dehydrogenation unit with an olefin conversion unit to convert butane feedstock to propylene and butadiene products. The combined catadiene-OCT process produces yields of propylene from normal butane in excess of 70%.

5 Claims, 2 Drawing Sheets

PRODUCTION OF PROPYLENE FROM BUTANE

This invention relates to an improved process for the production of olefins in an industrial chemical process and more particularly to an improved process for the production of propylene and butadiene from $C_4$ streams comprising butane.

BACKGROUND

High purity olefins, such as propylene and butadiene, have traditionally been produced through the process of steam and/or catalytic cracking. For example, propylene is usually produced as one of the main by-products in an ethylene plant or as a secondary by-product in a refinery utilizing a fluid catalytic cracker. Because of the limited efficiency of existing industrial systems and the high cost of petroleum sources, the cost of producing high purity olefins has been steadily increasing.

Polymer-grade propylene is required for the production of polypropylene and useful for the production of other propylene derivatives. Polymer-grade propylene is characterized by very low concentrations of impurities, including low levels of paraffins (saturated hydrocarbons) such as propane, ethane, and butane. Commercial chemical-grade propylene, unlike polymer-grade propylene, is characterized by higher concentrations of saturated hydrocarbons. Typical chemical-grade propylene purities range from 95% to 99.0% propylene, and for polymer grade propylene the purity is typically above 99.5%.

Another olefin that is often produced in commercial chemical plants is butadiene. Butadiene is a versatile raw material used in the production of a wide variety of synthetic rubbers, polymer resins and chemical intermediates. The largest uses for butadiene are the production of styrene butadiene rubber and polybutadiene rubber, which are used mainly in tire products. Butadiene is also one of the components used in the manufacture of acrylonitrile-butadiene-styrene, styrene-butadiene copolymer latex, styrene-butadiene block copolymers and nitrile rubbers.

Processes for direct propylene production include technologies directed specifically to conversion of $C_4$ hydrocarbons to propylene, such as Olefins Conversion Technology (OCT) from Lummus Technology, Inc. and the CATOFIN® dehydrogenation process. In the OCT process, n-butenes from $C_4$ feed are reacted with ethylene to produce polymer-grade propylene in a fixed bed catalytic metathesis reactor. The catalyst promotes two primary chemical reactions in the OCT process: (1) propylene is formed by metathesis of ethylene and 2-butene; and (2) 1-butene is isomerized to 2-butene as 2-butene is consumed in the metathesis reaction. The CATOFIN® dehydrogenation process uses a fixed-bed reactor having a catalyst selected to optimize conversion of propane to propylene.

Other methods of propylene production have been described. For example, U.S. Pat. No. 6,420,619 describes the production of propylene using successive distillation, hydrogenation and isomerization of a $C_3$-$C_6$ hydrocarbon cut from a cracking process to form 2-butene. Thereafter, the 2-butene is catalytically metathesized with ethylene to form propylene. U.S. Pat. No. 7,074,976 describes the production of propylene from olefins using a combination of hydrogenation, isomerization and disproportionation to form internal linear olefins. Thereafter, the internal linear olefins are converted to propylene.

Butadiene can be produced using the CATADIENE® process. This technology is a single step process for catalytic dehydrogenation of light hydrocarbons to produce diolefins of the same carbon number. Using the CATADIENE® process $C_4$ feedstocks may be converted to butadiene. Other butadiene production processes have been described. For example, U.S. Pat. No. 7,417,173 describes the production of butadiene from n-butane using dehydrogenation, condensation and phase separation to produce a product stream consisting substantially of butadiene.

None of the processes for production of propylene or butadiene discussed above describe the conversion of low value feedstocks comprising butane to produce both propylene and butadiene. There exists an ongoing and unmet need in the industry for improved, economical and efficient methods for producing olefins, such as propylene and butadiene, in industrial chemical processes. The present invention overcomes the deficiencies of the prior art by producing both propylene and butadiene in an integrated process.

SUMMARY OF THE INVENTION

This invention relates to an improved process for the production of olefins in an industrial chemical process, and more particularly to an improved process for the production of propylene and butadiene from $C_4$ streams mainly comprising butane.

In one aspect, the present invention is directed to a process for producing olefins comprising the steps of providing a feedstock comprising butane. The butane feedstock is introduced into a dehydrogenation unit capable of converting butane to butenes and butadiene, such as for example a CATADIENE® dehydrogenation unit, to produce a dehydrogenation unit product stream. The product stream from the dehydrogenation unit comprises butadiene and butenes. Butadiene is separated from the butenes, for example in a butadiene extraction unit, to produce a raffinate stream comprising butenes and residual butadiene. The butenes in the raffinate stream are fed to an olefin conversion unit, such as for example an OCT unit, where the 2-butenes in the stream are combined with ethylene and converted to propylene. The propylene product may be separated from unreacted butenes and butanes in a debutanizer and the separated butenes and butanes may be recycled back to the dehydrogenation unit to improve the overall yield of the process.

To increase the yield of propylene from the process, the raffinate stream comprising butenes and residual butadiene may be further treated to convert the residual butadiene to butenes. In this embodiment of the invention, the raffinate stream is fed to a selective hydrogenation unit (SHU) which contains a selective catalyst to promote conversion of butadiene to normal butenes. Optionally, a deoiler may be included prior to the SHU to remove any heavy $C_5$+ tails that may be present in the raffinate stream.

The effluent from the SHU may be fed to a deisobutanizer unit to separate isobutane and isobutene that may be present in the stream from the butenes. The butenes from the SHU unit are then fed to the olefin conversion unit, where the 2-butenes in the stream are combined with ethylene and converted to propylene. The propylene product may be separated from unreacted butenes and butanes in a debutanizer and the separated butenes and butanes may be recycled back to the dehydrogenation unit to improve the overall yield of the process as described above.

The process of the present invention allows conversion of low value butane feedstock to high value butadiene and propylene products. The synergy of producing normal butenes from normal butanes and then utilizing the normal butenes in a highly selective metathesis process, such as in an OCT unit, results in lower capital investment, low energy consumption and a high yield route to produce propylene. The process has better economics compared to thermal cracking of butanes in which the yield of propylene from normal butane is only about 15 to 20%. The process of the present invention can result in yields as high as 70-72%. These advantages are given by way of non-limiting example only, and additional benefits and additional advantages will be apparent to those skilled in the art in view of the description set forth herein.

DETAILED DESCRIPTION OF THE INVENTION

This invention relates to an improved process for the production of olefins in an industrial chemical process and more particularly to an improved process for the production of propylene and butadiene from $C_4$ feedstocks and streams comprising butane. The process converts feedstocks comprising butane into propylene and butadiene products by the integration of a dehydrogenation unit with an olefin conversion unit for converting butene to propylene.

The process described below may be used to convert feed streams comprising butane into butadiene and propylene. In one embodiment of the process, the feed stream comprising butane is first sent to a dehydrogenation unit where the butane is converted to butadiene and butenes. The butadiene in the product stream from the dehydrogenation unit is extracted from the product stream in a butadiene extraction unit. The raffinate from the butadiene extraction unit comprising butenes and residual butadiene is fed to an olefin conversion unit, where the 2-butenes in the stream are combined with ethylene and converted to propylene. The propylene product may be separated from unreacted butenes and butanes in a debutanizer and the separated butenes and butanes may be recycled back to the dehydrogenation unit to improve the overall yield of the process.

In another embodiment of the process, the raffinate stream from the butadiene extraction unit comprising butenes and residual butadiene is further treated to convert the residual butadiene to butenes. In this embodiment of the invention, the raffinate stream is fed to a selective hydrogenation unit (SHU) which contains a selective catalyst to promote conversion of butadiene to butene. Optionally, a deoiler may be included prior to the SHU to remove any heavy $C_5+$ tails that may be present in the raffinate stream.

The effluent from the SHU may be fed to a deisobutanizer unit to separate and remove isobutane and isobutene that may be present in the stream from the butenes in the stream. The stream containing butenes is then fed to the olefin conversion unit, where the 2-butenes in the stream are combined with ethylene and converted to propylene. The propylene product may be separated from unreacted butenes and butanes in a debutanizer and the separated butenes and butanes may be recycled back to the dehydrogenation unit to improve the overall yield of the process.

As used herein, the term "butane(s)" refers to all saturated $C_4$ chemical compounds, such as n-butane and isobutane.

As used herein, the term "butene(s)" refers to all singularly unsaturated $C_4$ chemical compounds, such as 1-butene, 2-butene and isobutene.

Figure 1:
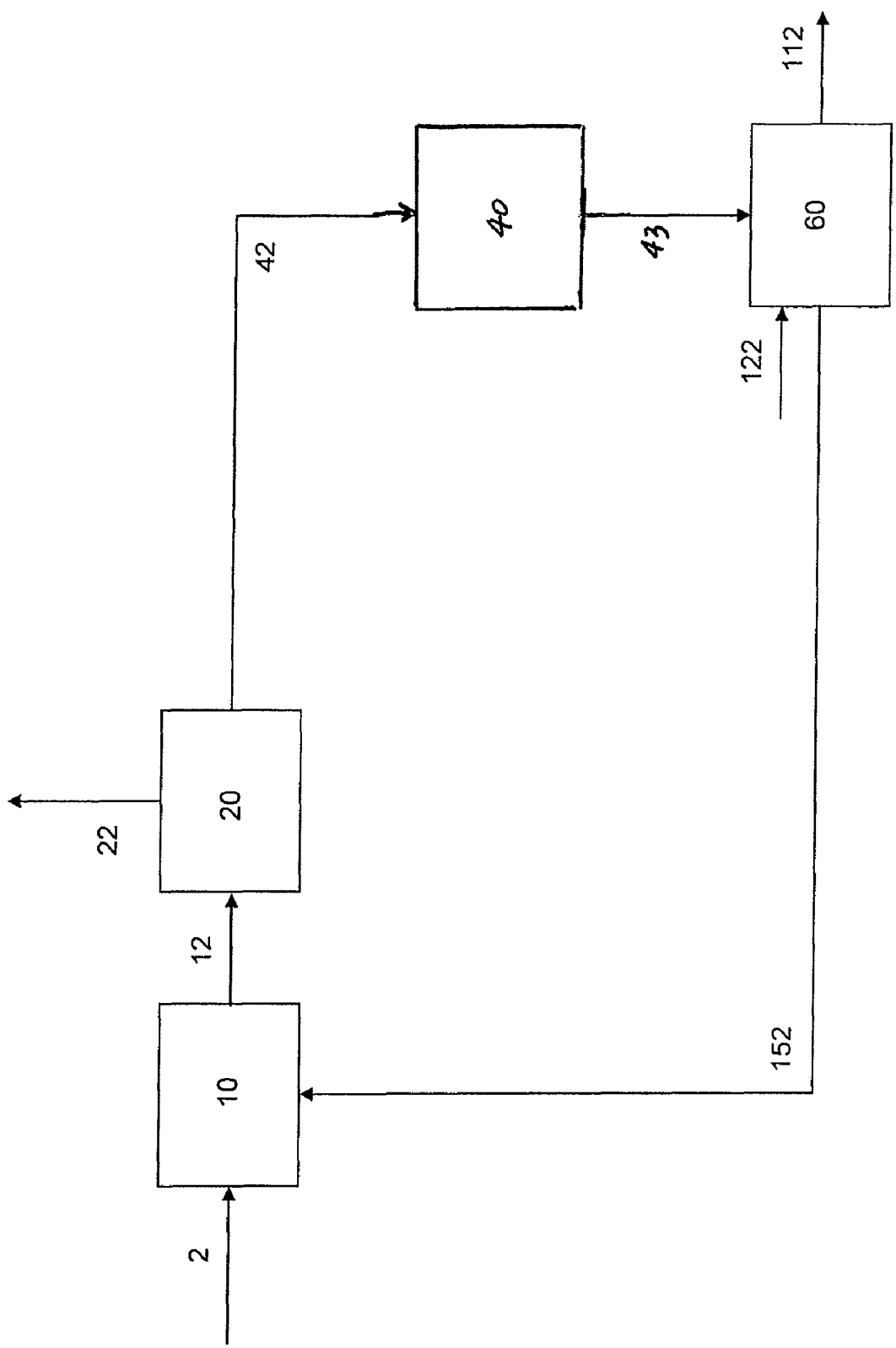
FIG. 1 is a diagram of one embodiment of the process of the present invention wherein a $C_4$ feedstock is processed using a dehydrogenation unit, a butadiene extraction unit and an olefin conversion unit.

FIG. 1 is a block diagram of one embodiment of the process of the present invention in which a feed stream comprising butane is processed using a CATADIENE® dehydrogenation unit, a butadiene extraction unit and an olefin conversion unit. The feed stream may be substantially pure butane or may contain other hydrocarbons, although the feed stream should typically contain butane as the primary hydrocarbon.

Referring to FIG. 1, the feed stream (2) is fed to a dehydrogenation unit (10) containing a catalyst for conversion of butane to butadiene and butene. The catalyst used in the dehydrogenation unit is typically a chromium/alumina catalyst, and may include a stream (152) comprising recycled, unreacted butane and butene may also be fed to the dehydrogenation unit (10) from an olefin conversion unit (60) described further below. The recycle stream (152) may be fed directly to the dehydrogenation unit (10) as shown in FIG. 1, or the recycle stream (152) may be combined with the feed stream (2) and the combined stream (not shown) is fed to the dehydrogenation unit (10). Any appropriate dehydrogenation unit and catalyst may be used in the process.

In one embodiment of the invention, the dehydrogenation unit is a CATADIENE® dehydrogenation unit. In the CATADIENE® process, butane is dehydrogenated over chromium/alumina catalysts. The dehydrogenation reactors typically operate at 12-15 cm Hg absolute pressure and approximately 1100-1260° F. (600-800° C.). Multiple reactors can be used to simulate continuous operation. Residence time in the reactor is approximately 5-15 minutes. Due to coke formation, the reactors must be periodically taken off-line and regenerated by burning the coke, typically using preheated air.

The effluent from the dehydrogenation reactor may be cooled and compressed and fed to a chilling and separation system to produce a stream high in $C_4$ components.

The product stream (12) from the dehydrogenation unit (10) is fed to a butadiene extraction unit (20). The butadiene extraction unit (20) separates high purity butadiene product from other hydrocarbons contained in the dehydrogenation unit product stream (12), such as butenes. The high purity butadiene is removed in stream (22) and sent for further processing or storage. The butadiene extraction unit (20) may be operated at a pressure range from just above atmospheric to about 10.0 barg with temperatures between 20-60° C.

The raffinate stream (42), comprised of butenes and residual butadiene, is fed from the butadiene extraction unit (20) to a selective hydrogenation unit ("SHU") (40) where the residual butadiene in the raffinate is converted to butenes. The SHU product stream (43) comprising the treated raffinate stream is combined with ethylene in the olefin conversion unit (60) and converted to propylene. Ethylene may be fed directly to the olefin conversion unit through stream (122) as shown in FIG. 1. Alternatively, ethylene may be combined with the SHU product stream (43) and the combined stream (not shown) may be fed to the olefin conversion unit (60) to produce a propylene product stream (112) and a recycle stream (152) comprising unreacted butenes.

In one embodiment of the invention, the olefin conversion unit is an Olefin Conversion Technology (OCT) unit from Lummus Technology, Inc. In an OCT unit, ethylene feed and butene feed are mixed and heated prior to being fed to a fixed-bed metathesis reactor. The catalyst used in the reactor promotes the reaction of ethylene and 2-butene to form propylene, and simultaneously isomerizes 1-butene to 2-butene.

The ethylene-to-butene ratio to the reactor is controlled at a value to minimize $C_5+$ olefin by-products from side reactions. Typical butene conversions range from about 55% to 75%, with greater than 90% selectivity to propylene.

In the OCT unit, the product from the metathesis reactor is cooled and fractionated in an ethylene column to remove ethylene for recycle. A small portion of this recycle stream is purged to remove methane, ethane and other light impurities from the process. The ethylene column bottoms are fed to a debutanizer column where unreacted butenes are separated from the propylene for recycle. The propylene product stream is sent for further processing or storage.

Figure 2:
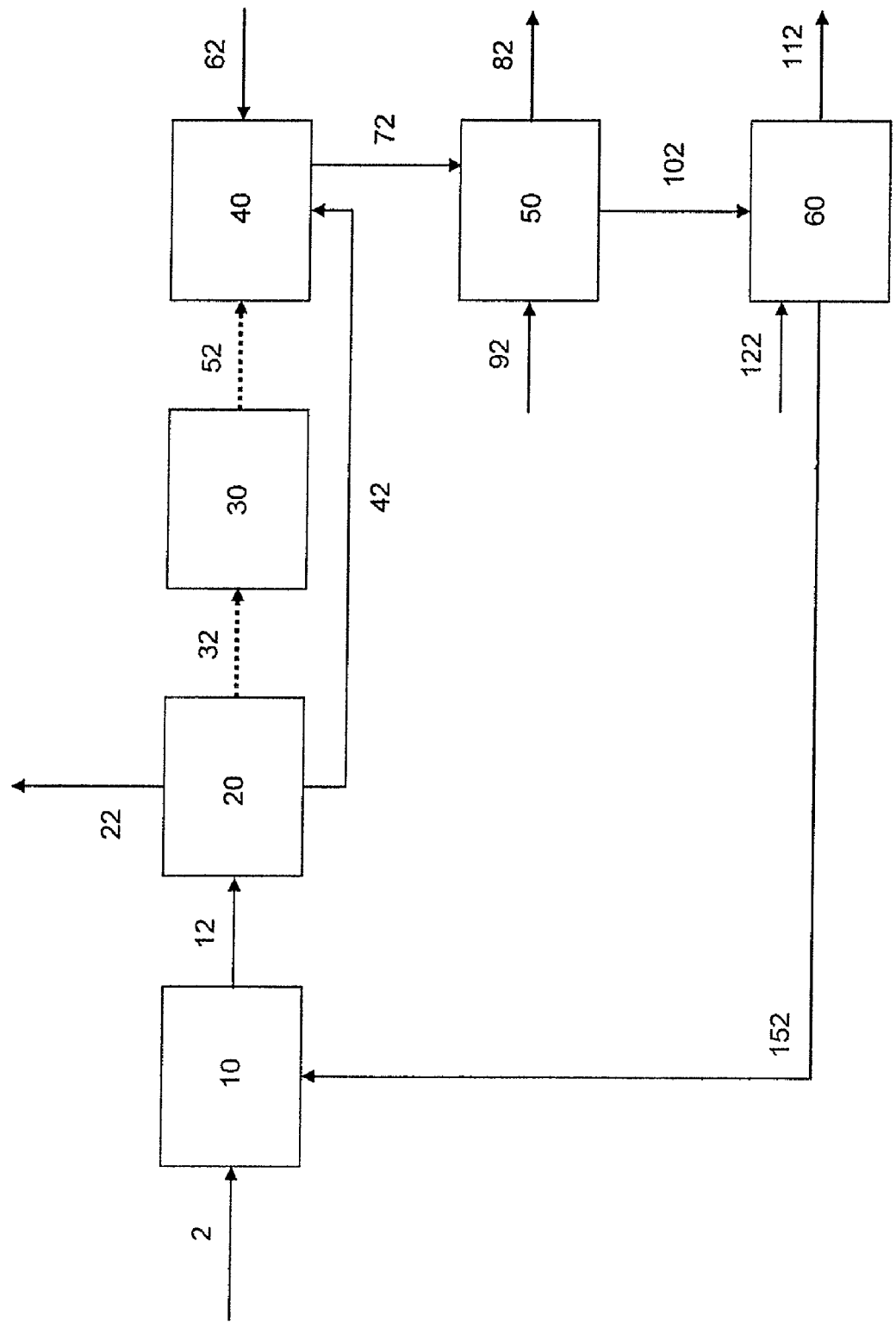
FIG. 2 is a diagram of one embodiment of the process of the present invention wherein a $C_4$ feedstock is processed using a dehydrogenation unit, a butadiene extraction unit, an optional deoiler, a $C_4$ hydrogenation unit, a deisobutenizer unit, an olefin conversion unit, and an optional debutanizer before being recycled.

FIG. 2 is a block diagram of another embodiment of the process of the present invention wherein a $C_4$ feed stream is processed using a CATADIENE® dehydrogenation unit, a butadiene extraction unit, an optional deoiler, a $C_4$ selective hydrogenation unit, a deisobutenizer unit, and an olefin conversion unit.

Referring now to FIG. 2, in this embodiment of the invention, a feed stream (2) comprising butane and a recycle stream (152) comprising unreacted butenes are fed to a dehydrogenation unit (10) as described above. In one embodiment, the dehydrogenation unit is a CATADIENE® dehydrogenation unit. The butane in the feed stream is converted to butadiene and butene as described above.

The product stream (12) from the dehydrogenation unit (10) is fed to a butadiene extraction unit (20) where butadiene is separated from butanes. The butadiene product stream (22) is sent for further processing or storage.

The butadiene extraction unit raffinate stream (42) and a hydrogen gas stream (62) are fed to a selective $C_4$ hydrogenation unit (SHU) (40). The streams are typically between about 6 to 17 barg pressure and between about 50 to 100° C. The hydrogen gas stream (62) may be fed directly to the SHU or it may be combined with the butadiene extraction unit product stream (42) prior to being fed to the SHU. Any appropriate hydrogenation reactor and catalyst for conversion of butadiene to butene may be used. The SHU (40) is typically a fixed bed reactor containing a catalyst capable of selectively converting the residual butadiene in the butadiene extraction unit raffinate stream (42) to butenes. The SHU (40) may be operated at about 6 to 17 barg pressure and between about 50 to 100° C.

Optionally, in another embodiment of the invention indicated by the dotted lines in FIG. 2, the butadiene extraction unit raffinate stream (32) may be fed to a deoiler unit (30) prior to being fed through line (52) to the SHU (40) operated as described above. The deoiler unit (30) removes any heavy $C_5+$ compounds that may be present in the butadiene extraction unit product stream prior to feeding the stream to the SHU. The deoiler unit effluent stream (52) is then fed to the SHU (40).

As shown in FIG. 2, the product stream (72) from the SHU (40) is thereafter fed into a deisobutenizer unit (50), such as, for example, a CD Hydro Deisobutenizer. Hydrogen gas (92) is also fed into the deisobutenizer unit (50). The deisobutenizer unit (50) separates isobutane and isobutene from the butenes in the feed stream to the unit. The isobutanes and isobutenes are removed through line (82). This unit also isomerizes 1-butene to 2-butene. The deisobutenizer unit (50) may be operated at a pressure between about 5 and 7 barg and a temperature of between 50 to 80° C.

The deisobutenizer unit product stream (102) is fed to an olefin conversion unit (60), such as for example the OCT unit discussed above. The deisobutenizer unit product stream (102) comprises butenes, butanes and trace amounts of butadiene. The 2-butenes in the deisobutenizer unit product stream are combined with ethylene in the olefin conversion unit and converted to propylene. Ethylene may be fed directly to the olefin conversion unit through stream (122) as shown in FIG. 2. Alternatively, ethylene may be combined with the deisobutenizer stream (102) and the combined stream (not shown) may be fed to the olefin conversion unit to produce a propylene product stream (112) and a recycle stream (152) comprising unreacted butenes and butanes. The recycle stream (152) is fed back to the dehydrogenation unit (10), and the propylene product stream (112) is sent for further processing or storage. In one embodiment of the invention, the olefin conversion unit is an Olefin Conversion Technology (OCT) unit from Lummus Technology, Inc.

The integrated dehydrogenation-olefin conversion system is capable of producing propylene and butadiene in higher yields than conventional systems. Preferably, the integrated dehydrogenation-olefin conversion unit can convert $C_4$ feedstocks comprising butane to propylene and butadiene wherein the yield of propylene and butadiene with respect to butane is greater than about 50% to 70% or more.

One skilled in the art will recognize that numerous variations or changes may be made to the process described above without departing from the scope of the present invention. Accordingly, the foregoing description of preferred embodiments and following examples are intended to describe the invention in an exemplary, rather than a limiting sense.

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

Example 1

The overall yield of an integrated system comprising a CATADIENE® dehydrogenation unit and an Olefin Conversion Technology (OCT) unit described above and shown in FIG. 2 was determined. A butane feed stream was fed to a CATADIENE® dehydrogenation unit to produce butadiene and butenes. The catadiene dehydrogenation unit product was then fed to a butadiene extraction unit wherein butadiene was separated from butenes and recovered.

The butadiene extraction unit product stream comprising butenes was then fed to a selective $C_4$ hydrogenation unit with hydrogen gas to convert any remaining butadiene to butenes. The selective $C_4$ hydrogenation unit product stream and a hydrogen gas stream were fed to a CD Hydro deisobutenizer unit. The CD Hydro deisobutenizer unit separated isobutane and isobutene from the butenes in the feed stream.

The CD Hydro deisobutenizer unit product stream and an ethylene feed stream were fed to an OCT unit. In the OCT unit, 2-butenes reacted with ethylene to produce polymer grade propylene. The propylene was separated from unreacted butene and recovered.

For a normalized butane feed of 100 lbs., the ethylene feed was 24 lbs. The normalized amount of propylene and butadiene (i.e., products) recovered from the system was 72 lbs. and 16 lbs. respectively, indicating that the total products/total feed yield ratio was 71%.

Example 2

The overall yield of a conventional n-butane cracker system was determined. Normal butanes were fed into a conventional cracker unit operated at typical conditions. The cracker unit produced both propylene and ethylene products. The propylene and ethylene were separated and recovered apart from the cracker unit product.

The normalized amount of butanes (i.e., feed) fed into the system was 100 lbs. The amount of propylene and ethylene (i.e., products) recovered from the system was 17 lbs. and 38 lbs., respectively. The overall total products/total feed yield ratio was 55%. The total product/feed yield of propylene was 17%.

Example 3

The overall yield of a conventional butadiene production system comprising a CATADIENE® dehydrogenation unit and a butadiene extraction unit was determined. Butanes were fed to a CATADIENE® dehydrogenation unit operated under typical conditions. The CATADIENE® dehydrogenation unit product was then fed into a butadiene extraction unit wherein butadiene was separated and recovered. Unreacted butanes or butenes were fed back into the CATADIENE® unit to maximize butadiene yield.

The normalized amount of butanes fed into the system was 100 lbs. The normalized amount of butadiene product recovered from the system was 58 lbs. The total product/feed yield of butadiene was 58%.

What is claimed is:

1. A process for producing olefins comprising the steps of:
   (a) feeding a stream comprising butane to a dehydrogenation unit containing a catalyst for converting butane to butenes and butadiene to produce a dehydrogenation unit product stream;
   (b) feeding the dehydrogenation unit product stream to a butadiene extraction unit to produce a butadiene product stream and a raffinate stream;
   (c) feeding the raffinate stream to a selective hydrogenation unit configured to convert butadiene to butene to produce a selective hydrogenation unit product stream;
   (d) feeding the selective hydrogenation unit product stream and a stream comprising ethylene to an olefin conversion unit to react the butenes with ethylene to form propylene; and
   (e) recovering the propylene.

2. The process of claim 1, further comprising the step of recycling unreacted butenes from the olefin conversion unit to the dehydrogenation unit.

3. A process for producing olefins comprising the steps of:
   (a) feeding a stream comprising butane to a dehydrogenation unit containing a catalyst for converting butane to butenes and butadiene to produce a dehydrogenation unit product stream;
   (b) feeding the dehydrogenation unit product stream to a butadiene extraction unit to produce a butadiene product stream and a raffinate stream comprising butenes and residual butadiene;
   (c) feeding the raffinate stream to a selective hydrogenation unit capable of converting the residual butadiene to butenes to produce a selective hydrogenation unit product stream;
   (d) feeding the selective hydrogenation unit product stream to a deisobutenizer capable of separating isobutane and isobutene from the hydrogenation unit product stream to produce an isobutane/isobutene stream and a deisobutenizer product stream;
   (e) feeding the deisobutenizer unit product stream and a feed stream comprising ethylene to an olefin conversion unit capable of reacting butenes with ethylene to form propylene to form an olefin conversion unit product stream; and
   (f) recovering propylene from the olefin conversion unit product stream.

4. The processes of claim 3, further comprising the step of:
   (g) feeding the raffinate stream to a deoiler unit capable of removing $C_{5+}$ hydrocarbons from the raffinate stream prior to feeding the raffinate stream to the selective hydrogenation unit.

5. The process of claim 3, further comprising the step of:
   (g) recycling unreacted butenes from the olefin conversion unit to the dehydrogenation unit.

* * * * *